United States Patent
Leu

(10) Patent No.: US 8,908,957 B2
(45) Date of Patent: Dec. 9, 2014

(54) METHOD FOR BUILDING RULE OF THUMB OF DEFECT CLASSIFICATION, AND METHODS FOR CLASSIFYING DEFECT AND JUDGING KILLER DEFECT BASED ON RULE OF THUMB AND CRITICAL AREA ANALYSIS

(75) Inventor: Iyun Leu, Hsinchu (TW)

(73) Assignee: Elitetech Technology Co.,Ltd., Hsinchu County (TW)

( * ) Notice: Subject to any disclaimer, the term of this patent is extended or adjusted under 35 U.S.C. 154(b) by 321 days.

(21) Appl. No.: 13/338,672

(22) Filed: Dec. 28, 2011

(65) Prior Publication Data

US 2013/0170733 A1 Jul. 4, 2013

(51) Int. Cl.
*G06K 9/00* (2006.01)

(52) U.S. Cl.
USPC ............................. 382/144; 382/145; 382/149

(58) Field of Classification Search
CPC ...................... G06T 2207/30148; G06T 7/001
USPC .................................................. 382/144–145
See application file for complete search history.

(56) References Cited

U.S. PATENT DOCUMENTS

| | | | | |
|---|---|---|---|---|
| 5,544,256 A * | 8/1996 | Brecher et al. | ................. | 382/149 |
| 6,092,059 A * | 7/2000 | Straforini et al. | ................. | 706/14 |
| 6,148,099 A * | 11/2000 | Lee et al. | ...................... | 382/149 |
| 6,246,787 B1 * | 6/2001 | Hennessey et al. | ........... | 382/141 |
| 6,292,582 B1 * | 9/2001 | Lin et al. | ........................ | 382/149 |
| 6,483,938 B1 * | 11/2002 | Hennessey et al. | ........... | 382/149 |
| 6,922,482 B1 * | 7/2005 | Ben-Porath | ................... | 382/149 |
| 7,142,992 B1 * | 11/2006 | Huet et al. | ....................... | 702/58 |
| 7,602,962 B2 * | 10/2009 | Miyamoto et al. | ............ | 382/149 |
| 7,987,150 B1 * | 7/2011 | Luu et al. | ......................... | 706/47 |
| 2010/0180239 A1 | 7/2010 | Leu | | |
| 2011/0082650 A1 | 4/2011 | Leu | | |

* cited by examiner

*Primary Examiner* — Utpal Shah
(74) *Attorney, Agent, or Firm* — Li & Cai Intellectual Property (USA) Office

(57) ABSTRACT

A method for building a rule of thumb of defect classification is illustrated. Multiple defect classification images with killer defects of examples and all material information of processes associated with the defect, the pattern, and the background are input into the fab tool. The fab tool obtains image characteristics, process characteristics, and image relativity characteristics of the defects, the pattern, and the background in each of the input images, wherein the input images comprises the defect classification images with killer defects of examples. The rule of thumb of the defect classification is built based on the process characteristics, the image characteristics, and the image relativity characteristics of the defects, the pattern, and the background in each of the input images.

4 Claims, 11 Drawing Sheets

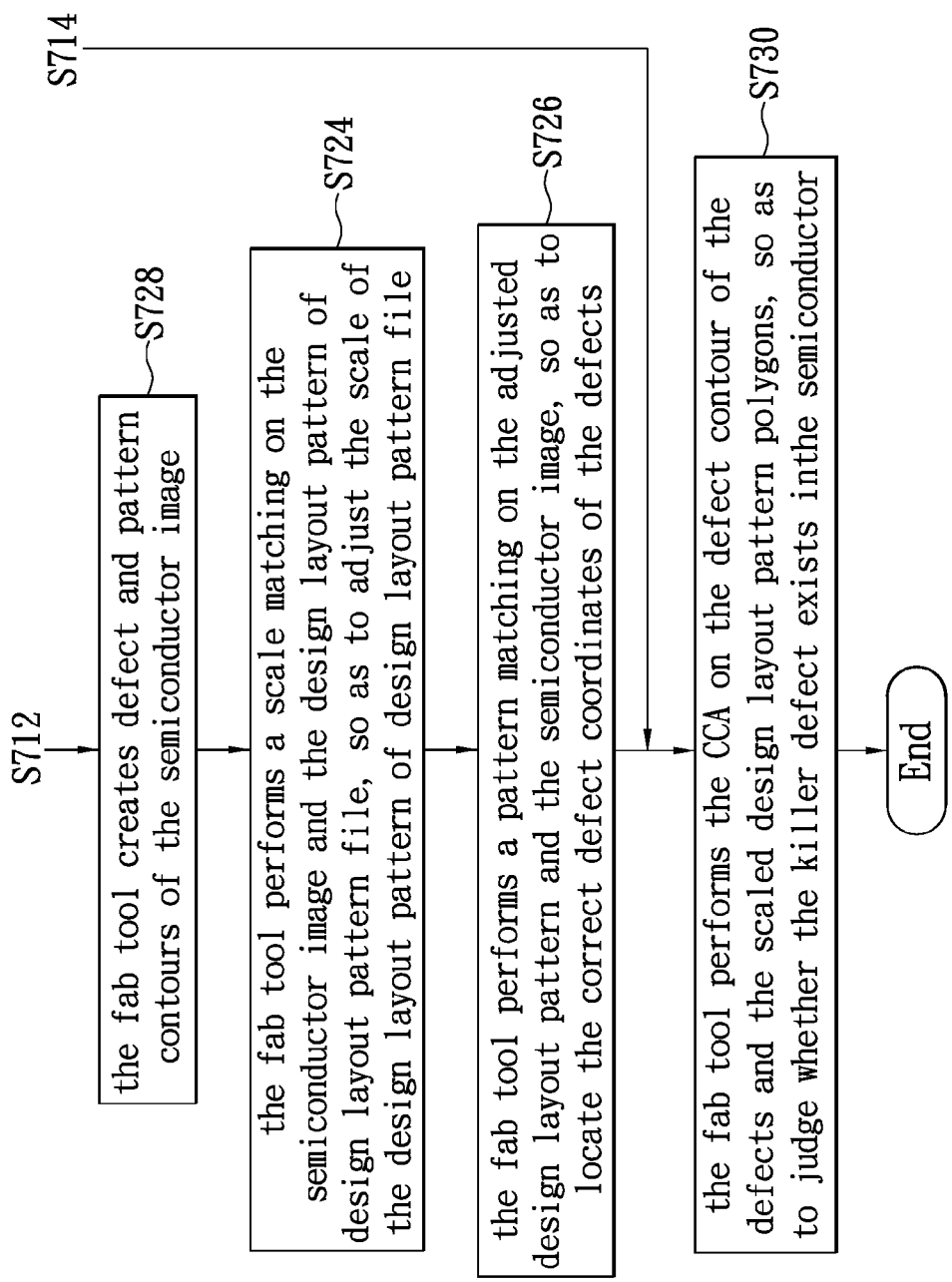

METHOD FOR BUILDING RULE OF THUMB OF DEFECT CLASSIFICATION, AND METHODS FOR CLASSIFYING DEFECT AND JUDGING KILLER DEFECT BASED ON RULE OF THUMB AND CRITICAL AREA ANALYSIS

BACKGROUND

1. Technical Field

The present disclosure relates to methods in a fab tool, and more particularly to a method for building a rule of thumb of the defect classification and methods for classifying the defect and judging the killer defect based on the rule of thumb and critical area analysis (CAA).

2. Description of Related Art

In the fab, during the semiconductor fabrication procedure, multiple processes is performed on the wafer, such priming, coating, baking, and photography processes. However, if at least a problem occurs during at least one of the processes, at least the defect is generated in the fabricated semiconductor. The defect which causes the failure of the fabricated semiconductor is called the killer defect. For example, two disconnected polygons of the pattern in the semiconductor may be shorted due to the defect, or the polygon of the pattern in the semiconductor may be separated into two disconnected polygons of the pattern due to the defect.

If the defect is the killer defect, the yield rate of the fabricated semiconductor is reduced. Fortunately, the dimension of the defect is little in the conventional semiconductor process technology, and thus the most defects are not the killer defects. However, the critical-dimension of the current semiconductor process technology is smaller than that of the conventional semiconductor process technology, and thus the defect of the semiconductor should not be neglected. Accordingly, the defect of the semiconductor should be detected, and whether the defect is the killer defect should be judged.

Referring to FIG. 1, FIG. 1 is a flow chart of a conventional method for classifying the defect and judging the killer defect. In the conventional method for classifying the defect and judging the killer defect, at step S100, the human must obtains a semiconductor image, wherein the semiconductor may have at least a defect. The semiconductor image may be photographed automatically by the scanning electron microscope (SEM), the optical microscope, or the e-beam microscope. Then, at step S102, the human must learn the typical defect type and the killer defect judgment knowledge. At step S104, the human observes at least the defect, the pattern, and the background in the semiconductor image by using his/her eyes. Next, at step S106, based on the typical defect type and the killer defect judgment knowledge, the human decides the defect type and judges whether the killer defect exists in the semiconductor according to the observation result of step S104.

Referring to FIG. 2, FIG. 2 is schematic view of a semiconductor image of an example. After the human observes the semiconductor image, the human may know that the semiconductor 2 includes a background 20, multiple polygons of a pattern 22, and defects 24. Then, based on the typical defect type and the killer defect judgment knowledge, the human will decide the each of defects 24 in the semiconductor 2 to be a short (or bridge) defect or an open defect. Both of the defects 24 are killer defects which cause the failure of the semiconductor 2.

When the killer defects of the semiconductor are judged frequently, the human must stop the semiconductor fabrication procedure, and adjust the process or equipment parameters of the processes, so as to assure the certain yield rate. The conventional method for classifying the defect and judging the killer defect can help to increase the yield rate, but it costs the fab exhaustive manpower.

SUMMARY

An exemplary embodiment of the present disclosure provides a method for building a rule of thumb of defect classification, applied in a fab tool, comprising: inputting multiple defect classification images with killer defects of examples into the fab tool; inputting all material information of processes associated with the defect, the pattern, and the background into the fab tool; performing an image detection on each of input images, so as to create image characteristics of the defects, the pattern, and the background in each of the input images, wherein the input images comprises the defect classification images with killer defects of examples; based on the image characteristics of the defects, the pattern, and the background in each of the input images, creating process characteristics and image relativity characteristics of the defects, the pattern, and the background in each of the input images; and building the rule of thumb of the defect classification based on the process characteristics, the image characteristics, and the image relativity characteristics of the defects, the pattern, and the background in each of the input images.

An exemplary embodiment of the present disclosure provides a method for classifying at least a defect based on a rule of thumb of defect classification built by the above method for building the rule of thumb of the defect classification, applied in the fab tool, comprising: inputting a semiconductor image into the fab tool, wherein the semiconductor image has at least a defect; inputting a defect scan data into the fab tool; loading the rule of thumb of the defect classification; performing an image detection and analysis on the input semiconductor image, so as to create the image characteristics of the defects, the pattern, and the background in the semiconductor image; based on the image characteristics of the defects, the pattern, and the background in the semiconductor image, creating process characteristics and image relativity characteristics of the defects, the pattern, and the background in the semiconductor image; and classifying the defects, the pattern, and the background of the semiconductor image based on the rule of thumb of the defect classification, so as to create the classification results of the defects of the semiconductor.

An exemplary embodiment of the present disclosure provides a method for judging a killer defect based on a rule of thumb of defect classification built by the above method for building the rule of thumb of the defect classification, applied in the fab tool, comprising: steps of the above method for classifying at least a defect based on the rule of thumb of the defect classification; inputting typical defect type and the killer judgment knowledge into the fab tool; based on the typical defect type and the killer judgment knowledge and the classification results of the defects, creating image pattern contours inside a defect area, image pattern contours outside the defect area, and a defect contour of the defects; recovering the image pattern contours inside the defect area; merging the recovered image pattern contours inside the defect area and the image pattern contours outside the defect area, so as to create image pattern contours of layout polygons; performing a critical area analysis based on the defect contour of the defects and the merged image pattern contours, so as to create a critical area analysis result; and judging whether the killer defect exists in the semiconductor according to the critical area analysis result.

A method for judging a killer defect based on a rule of thumb of defect classification built by the above method for building the rule of thumb of the defect classification, applied in the fab tool, comprising: steps of the above method for classifying at least a defect based on the rule of thumb of the defect classification; inputting a design layout pattern file into the fab tool; creating image pattern and defect contours; performing a scale matching on the semiconductor image and the design layout pattern of design layout pattern file, so as to adjust a scale of the design layout pattern of design layout pattern file; performing a pattern matching on the adjusted design layout pattern and the semiconductor image, so as to locate correct defect coordinates of the defects; and performing a critical area analysis on the defect contour of the defects and the scaled design layout, so as to judge whether the killer defect exists in the semiconductor.

To sum up, these methods can be applied in the fab tool, and thus the fab can increase efficiency and throughput several times and reduce yield learning cycle time, while the fab classifies the defects and judges the killer defect. Furthermore, the methods for judging the killer defect based on the rule of thumb and contour pattern critical area analysis can be performed regardless of the design layout pattern file.

In order to further understand the techniques, means and effects the present disclosure, the following detailed descriptions and appended drawings are hereby referred, such that, through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

Referring to FIG. 7A and FIG. 7B, FIG. 7A and FIG. 7B are respectively the upper part and the lower part of the flow chart of a method for judging the killer defect based on the built rule of thumb of the defect classification and CAA according to an exemplary embodiment of the present disclosure.

DESCRIPTION OF THE EXEMPLARY EMBODIMENTS

Figure 1:
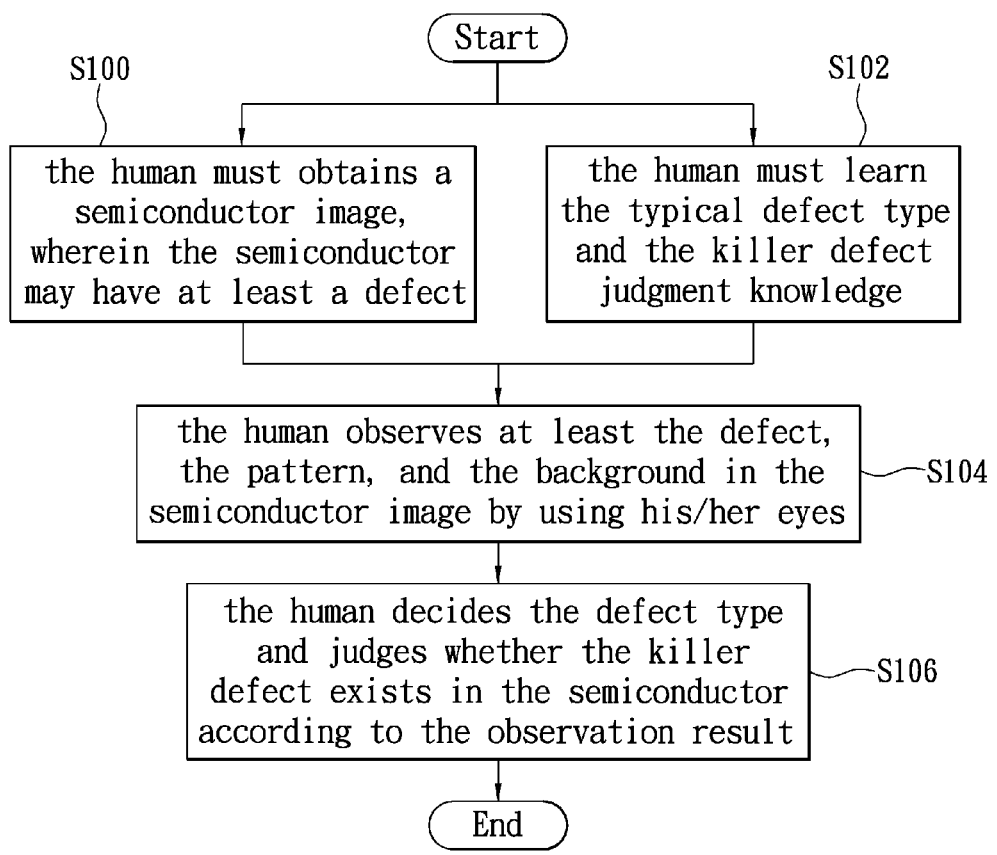
FIG. 1 is a flow chart of a conventional method for classifying the defect and judging the killer defect.

Reference will now be made in detail to the exemplary embodiments of the present disclosure, examples of which are illustrated in the accompanying drawings. Wherever possible, the same reference numbers are used in the drawings and the description to refer to the same or like parts.

An exemplary embodiment of the present disclosure provides a method for building a rule of thumb of the defect classification. Other exemplary embodiments of the present disclosure further provide methods for classifying the defect and judging the killer defect based on the rule of thumb and CAA. These methods can be applied in the fab tool, such as the fab tool used in the semiconductor, assembly fab, printed-circuit board (PCB) fab, solar cell fab, flat panel fab, mask fab, and light-emitting diode (LED) fab, and the fab tool is executed in a device with the computing ability. Compared to the conventional method, these methods can increase efficiency and throughput several times and reduce yield learning cycle time, thus the production cost is therefore reduced.

Figure 3:
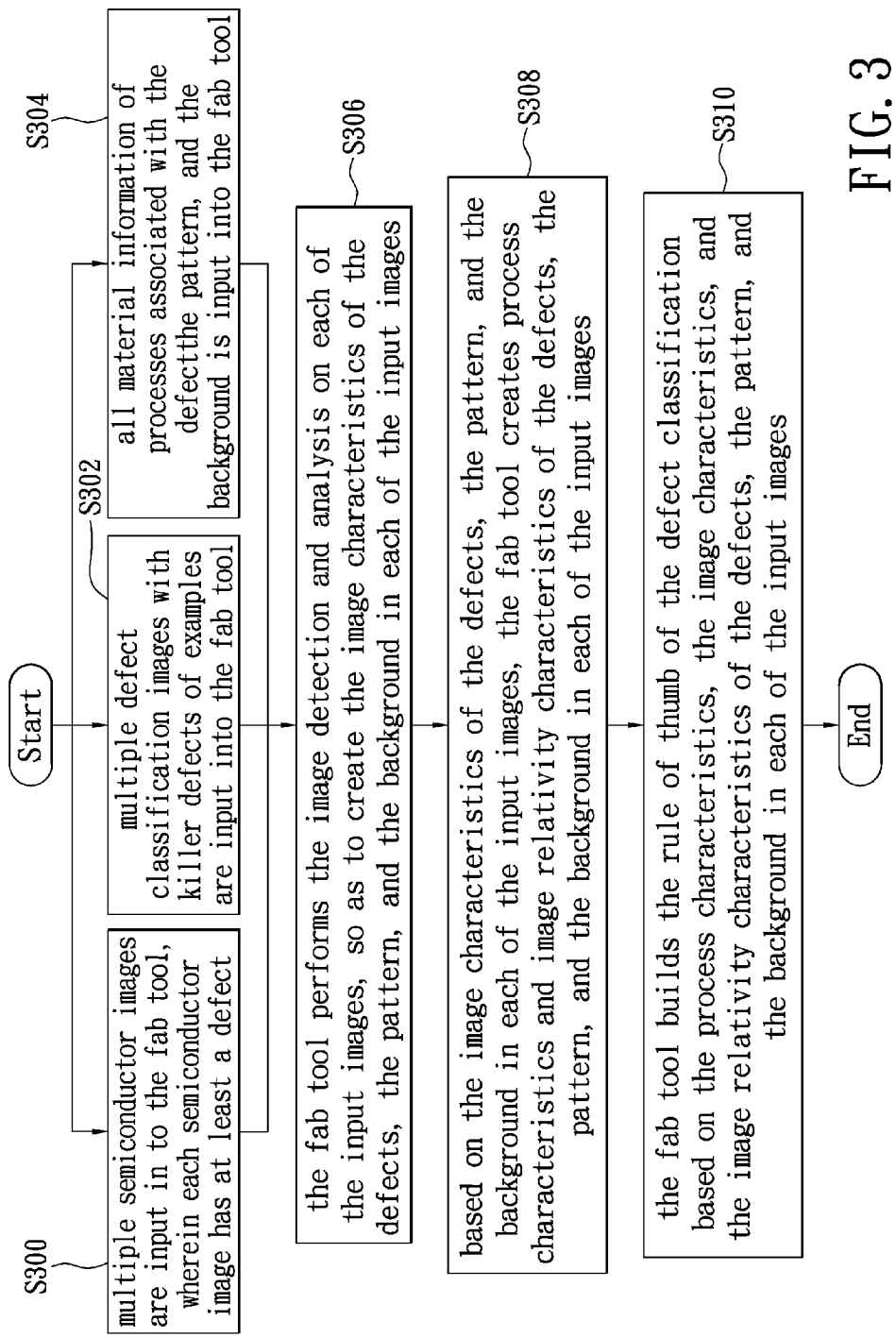
FIG. 3 is flow chart of a method for building a rule of thumb of the defect classification according to an exemplary embodiment of the present disclosure.

Referring to FIG. 3, FIG. 3 is flow chart of a method for building a rule of thumb of the defect classification according to an exemplary embodiment of the present disclosure. Before the fab tool automatically classifies the defect type and judges the killer defect, the rule of thumb of the defect classification is automatically built by the fab tool. Then, the methods for classifying the defect and judging the killer defect can be performed based on the rule of thumb and CAA, so as to decide the defect type and judge whether the killer defect exists in the semiconductor.

At step S300, multiple semiconductor images are input into the fab tool, wherein each semiconductor image has at least a defect. The multiple semiconductor images are photographed by the scanning electron microscope (SEM), the optical microscope, or the e-beam microscope. At step S302, multiple defect classification images with killer defects of examples are input into the fab tool. At step S304, all material information of processes associated with the defect, the pattern, and the background is input into the fab tool, wherein the material may be poly silicon or metal, and the metal is for example the copper.

It is noted, if the rule of thumb built based on the defect classification images with killer defects of examples is sufficient to classify all defects of different types, step S300 can be removed. However, to assure the precision of the defect classification and the killer defect judgment, the rule of thumb is preferred to be built based on the predefined defect classification images with killer defects of examples and the semiconductor images of step S300.

At step S306, the fab tool performs the image detection and analysis on each of the input images (the input images comprises the defect classification images with killer defects of examples and the input semiconductor images), so as to create the image characteristics of the defects, the pattern, and the background in each of the input images. The image detection and analysis results of the defects, the pattern, and the background in each of the input image are the image characteristics of the defects, the pattern, and the background in each of the input image. The material information of the processes associated with the defect, the pattern, and the background is used to indicate the fab tool to perform a proper image recognition process, since the different materials and processes may have different image characteristics, such the different brightness and the different polygon shape. For example, the brightness of the copper metal is bright, and the brightness of the hole or via is dark.

The implementation of the image detection and analysis process described as follows is not used to limit the present disclosure. The image recognition process comprises at least one of the edge detection, the noise filtering, the threshold analysis, the feature detection, the image scale detection, the contour cutting, the feature shape analysis, the contour generation, the pattern matching, the masking, the logic operation, the character recognition, the focus/defocus analysis, the light source detection, the color detection, and the texture analysis with the gray level co-occurrence matrix (GLCM).

The edge detection may be the discrete cosine transformation (DCT) detection, Sobel detection, or Canny detection. The noise filtering may be the low pass filtering, the bandpass filtering, the median filtering, Despeckle filtering, or the fit polynomial filtering. The threshold of the threshold comparison may be the histogram distribution analysis threshold, Otsu threshold, the local histogram distribution analysis threshold, or the binary threshold. The feature detection may be edge detection mentioned above and line detection through Hough transform. The image scale detection may be the field of view (FOV), the scale bar, and the image pixel size for scale recognition. The contour cutting may be the image feature segmentation. The feature shape analysis may be circular, oval, and rectangular shape detection. The contour generation may be contour tracing. The pattern matching may be the bitmap pattern matching, the corner pattern matching, or the vertices pattern matching. The logic operation may be the combination chosen from at least one of the adding, subtraction, inverse, log, and exponential operations. The character recognition may be the optical character recognition. The focus/defocus analysis may be the Gaussian blurring or Wiener filtering. The color detection may be the RGB analysis.

At step S308, based on the image characteristics of the defects, the pattern, and the background in each of the input images, the fab tool creates process characteristics and image relativity characteristics of the defects, the pattern, and the background in each of the input images.

The types of the process characteristics of defects, the pattern, and the background are not used to limit the present disclosure. The process characteristics comprise at least one of the material source, the position, the brightness, the shape, the size, the edge, the shadow, the roughness, the hardness, the direction, and so on. For example, the material source of the defect may be the pattern material, the background material, or the particle, and the material sources of the pattern and the background are of course respectively the pattern material and the background material.

The types of the image relativity characteristics of defects, the pattern, and the background are not used to limit the present disclosure. The image relativity characteristics comprise at least one of the relative position, the relative brightness, the relative smoothness, the top view image, the side view image, the pattern edge visibility in the defect site, the occurrence preferred location, the previous pattern shape, and so on. For example, the relative position of the defect to the pattern may be upper, lower, or the same, the relative position of the defect to the background may be upper, lower, or the same, and the relative position of the pattern to the background may be upper, lower, or the same.

At step S310, the fab tool builds the rule of thumb of the defect classification based on the process characteristics, the image characteristics, and the image relativity characteristics of the defects, the pattern, and the background in each of the input images. The different defects have the different process characteristics, the different image characteristics, and the different image relativity characteristics, and thus the fab tool gives the different defects with the different specific identification codes. By the similar manner, the fab tool gives the different patterns and the different backgrounds with the different specific identification codes. The rule of thumb of the defect classification records the specific identification codes of the defects, the patterns, the backgrounds, and their corresponding process characteristics, the specific image characteristics, and the specific image relativity characteristics.

That is, the specific identification code of the defect in the rule of thumb the defect classification is presenting of the defect with the specific process characteristics, the specific image characteristics, and the specific image relativity characteristics. By the similar manner, the specific identification code of the pattern in the rule of thumb the defect classification is presenting of the pattern with the specific process characteristics, the specific image characteristics, and the specific image relativity characteristics, and the specific identification code of the background in the rule of thumb the defect classification is presenting of the background with the specific process characteristics, the specific image characteristics, and the specific image relativity characteristics.

Figure 4:
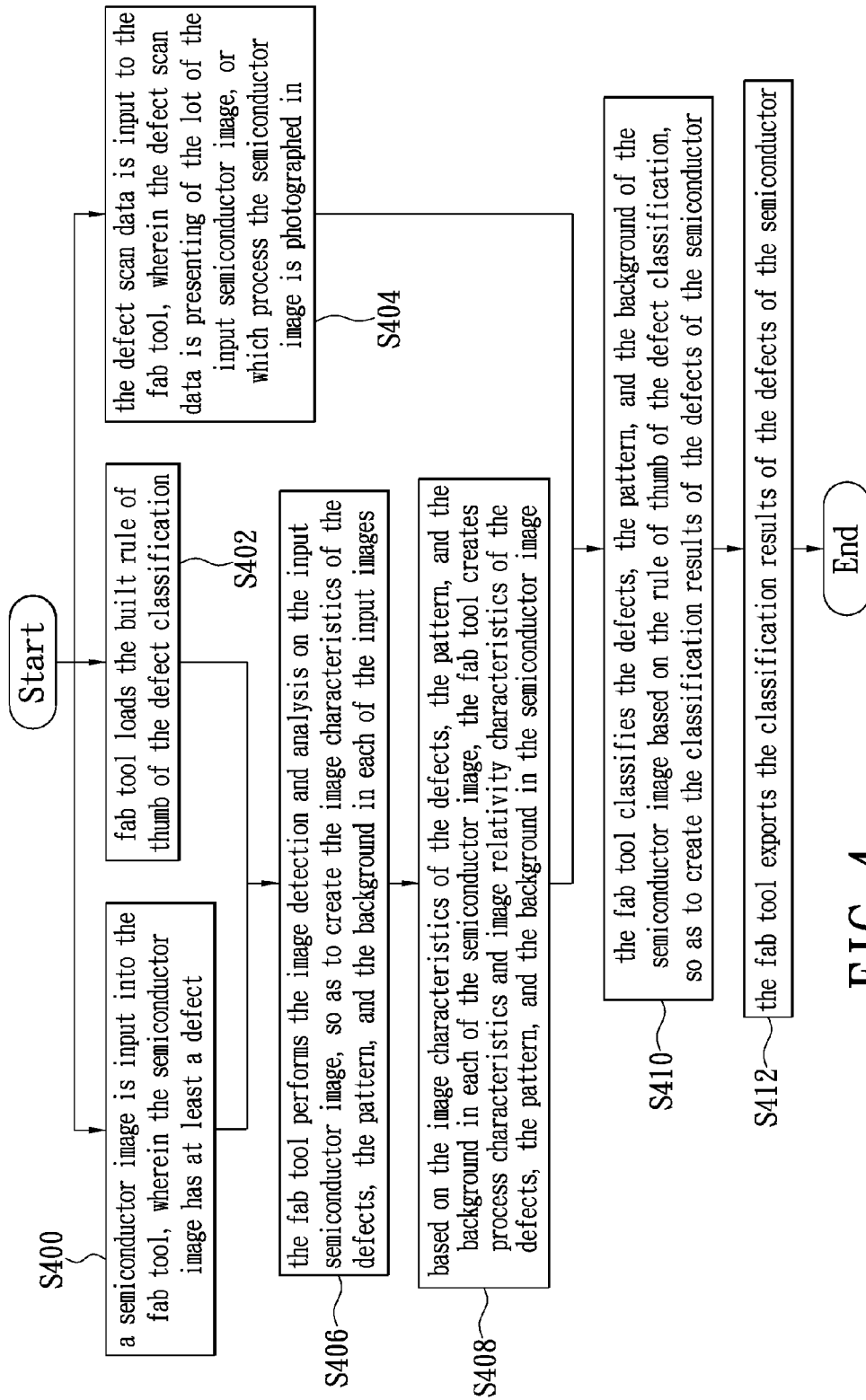
FIG. 4 is flow chart of a method for classifying the defect based on the built rule of thumb of the defect classification according to an exemplary embodiment of the present disclosure.

Referring to FIG. 4, FIG. 4 is flow chart of a method for classifying the defect based on the built rule of thumb of the defect classification according to an exemplary embodiment of the present disclosure. The fab tool using the method for classifying the defect based on the built rule of thumb of the intelligent defect classification can automatically classify the defects, the pattern, and the background of the semiconductor.

At step S400, a semiconductor image is input into the fab tool, wherein the semiconductor image has at least a defect. At step S402, the defect scan data is input to the fab tool, wherein the defect scan data is presenting of the lot of the input semiconductor image, or which process the semiconductor image is photographed in. Thus, after the fab tool creates the classification results, the classification results with lot and process identity can be known by the fab tool user. At step S404, the fab tool loads the built rule of thumb of the defect classification.

At step S406, the fab tool performs the image detection and analysis on the input semiconductor image, so as to obtain the image characteristics of the defects, the pattern, and the background in the input semiconductor image. Then, at step S408, based on the image characteristics of the defects, the pattern, and the background in the semiconductor image, the fab tool creates process characteristics and image relativity characteristics of the defects, the pattern, and the background in the semiconductor image.

Then, at step S410, the fab tool classifies the defects, the pattern, and the background of the semiconductor image based on the rule of thumb of the defect classification, so as to create the classification results of the defects of the semiconductor. Next, at step S412, the fab tool exports the classification results of the defects of the semiconductor to the fab tool user or to a storage device.

The fab tool compares the process characteristics, the image characteristics, and the image relativity characteristics of the defects in the semiconductor to all of the process characteristics, the image characteristics, and the image relativity characteristics of the defects in the rule of thumb of the defect classification, so as to find the similar defects in the rule of thumb of the defect classification. Then, the fab tool assigns the defects with the specific identification codes the same as those of the similar defects in the rule of thumb of the defect classification. By the similar manner, the fab tool assigns the pattern and the background with the specific identification codes the same as those of the similar pattern and the background in the rule of thumb of the defect classification. The assigned specific identification codes are the contents of the classification results of the defects.

It is noted that, the method for classifying the defect based on the built rule of thumb of the defect classification may further includes the step as follows. If one of the specific identification codes of the defects is the specific identification code of the killer defect, the fab tool can roughly judges the killer defect exists in the semiconductor. However, in the next description, other methods for judging the killer defect are provided.

Figure 5A:
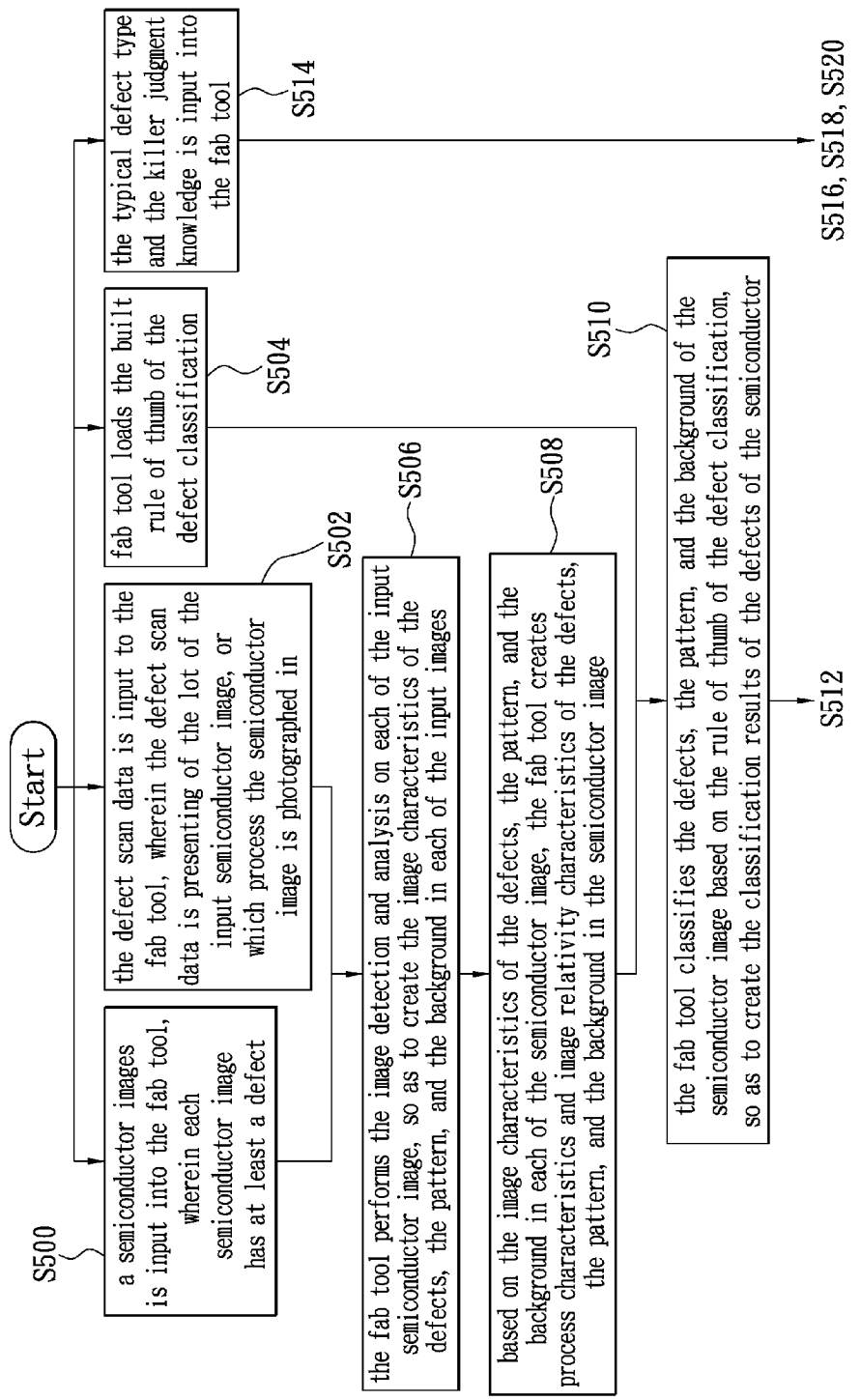
FIG. 5A and FIG. 5B are respectively the upper part and the lower part of the flow chart of a method for judging the killer defect based on the built rule of thumb of the defect classification and CAA according to an exemplary embodiment of the present disclosure.
Figure 5B:
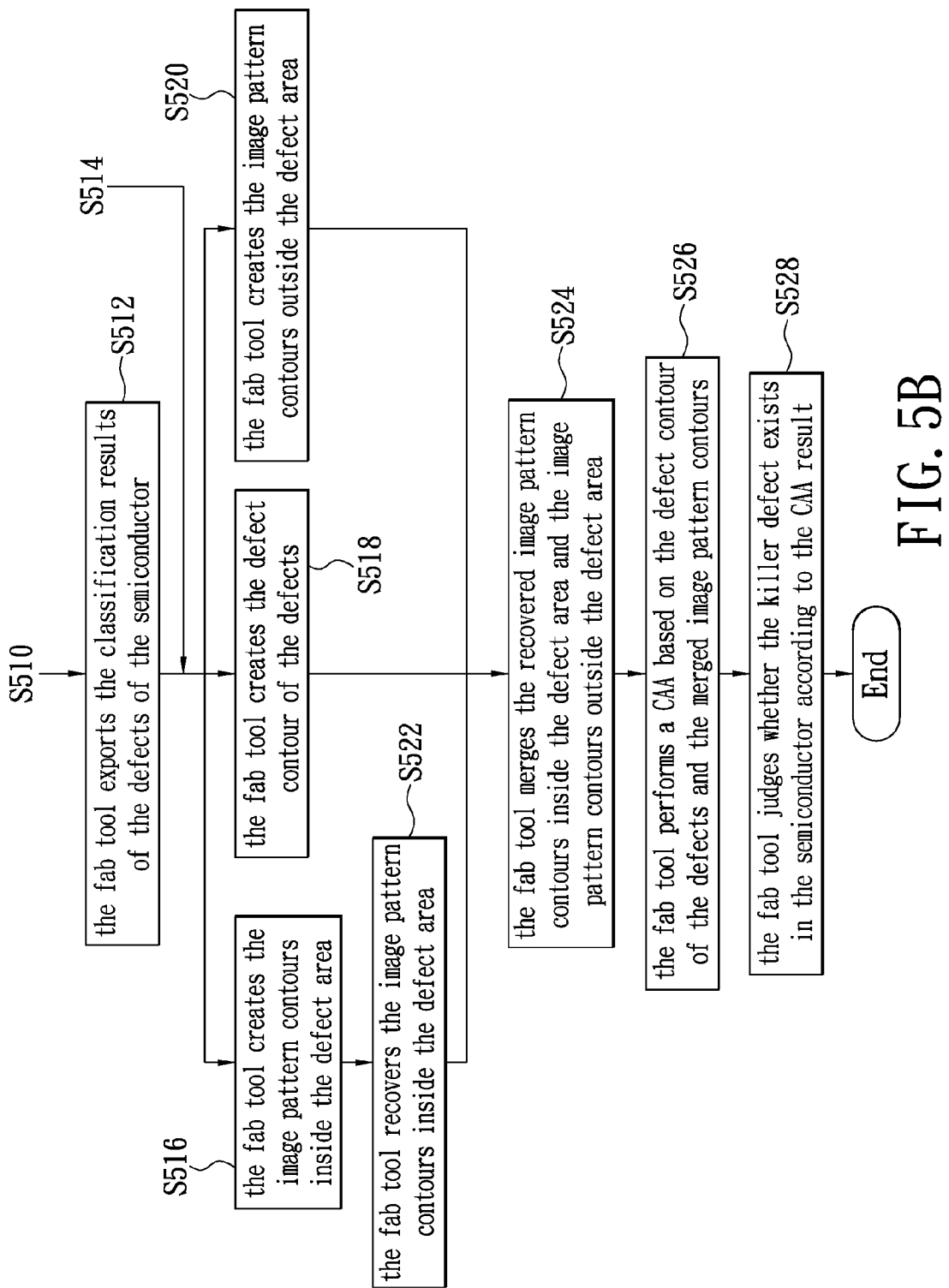

Referring to FIG. 5A and FIG. 5B, FIG. 5A and FIG. 5B are respectively the upper part and the lower part of the flow chart of a method for judging the killer defect based on the built rule of thumb of the defect classification and CAA according to an exemplary embodiment of the present disclosure. The defects of the semiconductor are firstly classified by the fab tool based on the built rule of thumb of the defect classification. Then, the classification results of the defects may be used to judge whether the killer defect exists in the semiconductor is judged according. In FIG. 5A, steps S500 through S512 are respectively the same as steps S400 through S412 of FIG. 4, and descriptions of steps S500 through S512 are thus omitted. At step S514, the typical defect type and the killer judgment knowledge is input into the fab tool.

In FIG. 5B, at step S516, based on the typical defect type and the killer judgment knowledge and the classification results of the defects, the fab tool creates the image pattern contours inside the defect area. At step S518, based on the typical defect type and the killer judgment knowledge and the classification results of the defects, the fab tool creates the defect contour of the defects, wherein the fab tool clips the defect contour of the defects from the semiconductor image so as to obtain the defect contour of the defects. At step S520, based on the typical defect type and the killer judgment knowledge and the classification results of the defects, the fab tool creates the image pattern contours outside the defect area.

At step S522, the fab tool recovers the image pattern contours inside the defect area. The details for recovering the image pattern contours inside the defect area will be illustrated with FIG. 5C, and herein the details of step S522 are omitted. At step S524, the fab tool merges the recovered image pattern contours inside the defect area and the image pattern contours outside the defect area. Next, at step S526, the fab tool performs CAA based on the defect contour of the defects and the merged image pattern contours of layout polygons. Then, at step S528, the fab tool judges whether the killer defect exists in the semiconductor according to the CAA result. That is, the CAA result records whether at least one of the defects causes the semiconductor failure. It is noted that the method for judging the killer defect based on the rule of thumb of the defect classification and CAA shown in FIG. 5 does not require the design layout pattern file.

Figure 5C:
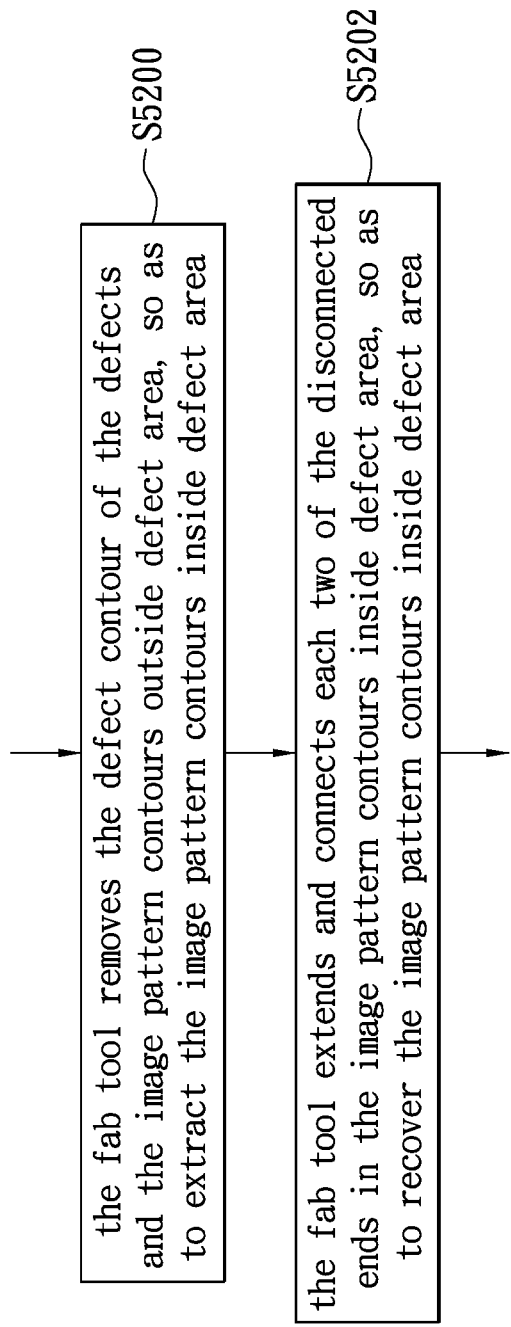
FIG. 5C is a flow chart of details of step S522 according to an exemplary embodiment of the present disclosure.

Referring to FIG. 5C, FIG. 5C is a flow chart of details of step S522 according to an exemplary embodiment of the present disclosure. At step S5200, the fab tool removes the defect contour of the defects and the image pattern contours outside defect area, so as to extract the image pattern contours inside defect area. Then, at step S5202, the fab tool extends and connects each two of the disconnected ends in the image pattern contours inside defect area, so as to recover the image pattern contours inside defect area similar to layout polygons.

Referring to FIG. 2 and FIG. 6A through FIG. 6D, FIG. 6A through FIG. 6D are schematic views respectively of the defect contour of the defects, the image pattern contours outside defect area, the image pattern contours inside defect area, and the recovered image pattern contours inside defect area according to an exemplary embodiment of the present disclosure.

Figure 2:
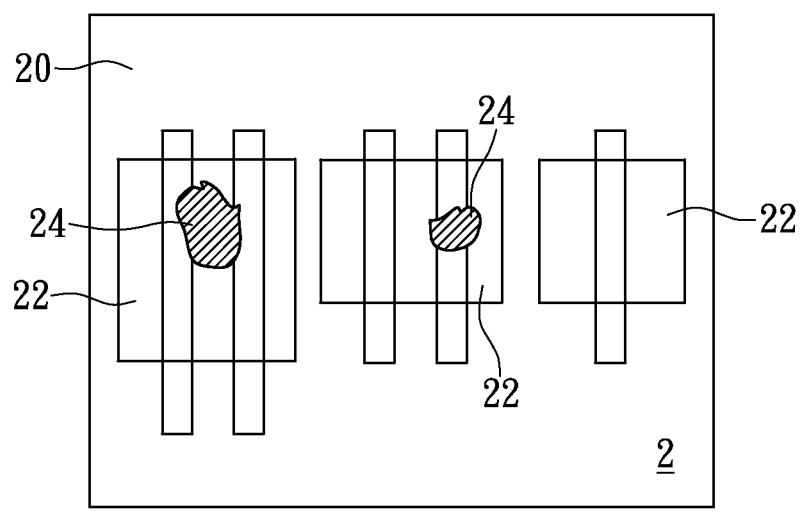
FIG. 2 is schematic view of a semiconductor image of an example.
Figure 6A:
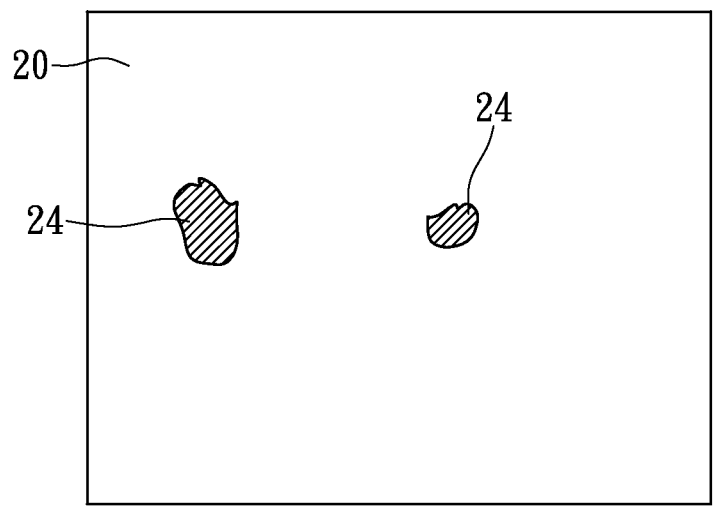
FIG. 6A through FIG. 6D are schematic views respectively of the defect contour of the defects, the image pattern contours outside defect area, the image pattern contours inside defect area, and the recovered image pattern contours inside defect area according to an exemplary embodiment of the present disclosure.
Figure 6B:
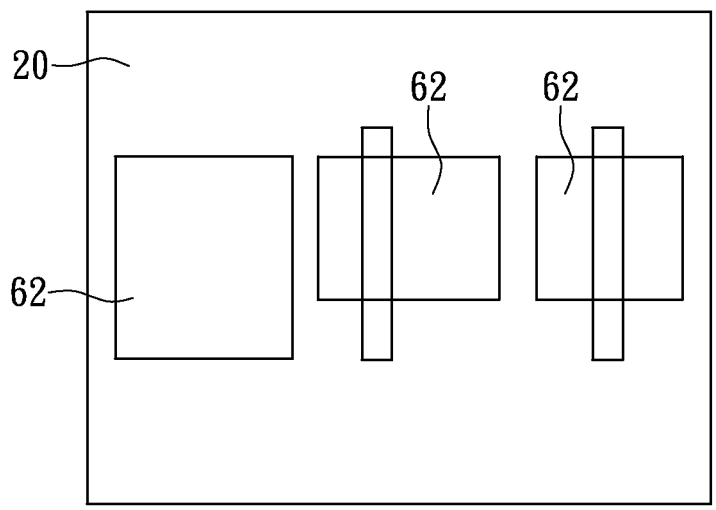
Figure 6C:
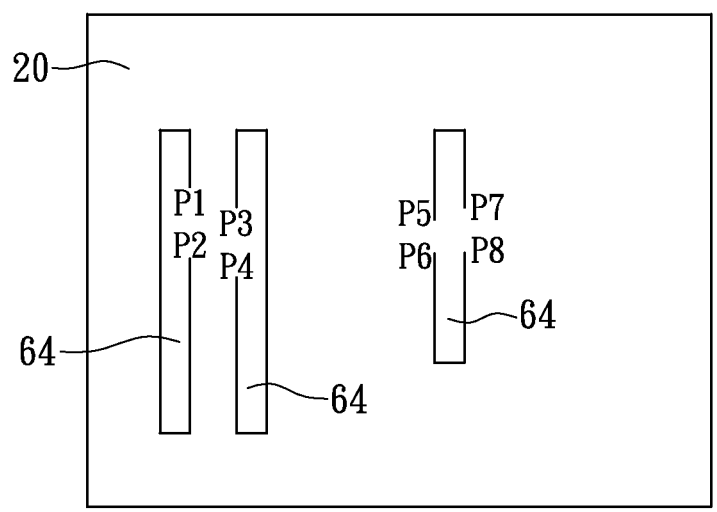
Figure 6D:
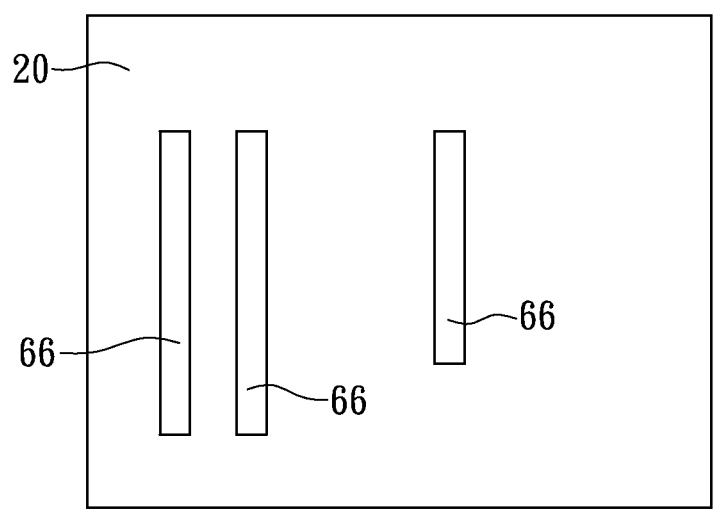

The fab tool clips the defect contour of the defects 24 of the semiconductor image shown in FIG. 2, and the clipped defect contour of the defects 24 shown in FIG. 6A is therefore obtained by the fab tool. The image pattern contours which are not overlapped by the defects are the image pattern contours 62 outside the defect area as shown in FIG. 6B. The image pattern contours which are overlapped by the defects are the image pattern contours 64 inside the defect area as shown in FIG. 6C. The fab tool extends and connects each two disconnected ends P1 through P8, so as to obtain the image pattern polygons 66 inside the defect area as shown in FIG. 6D.

Figure 7A:
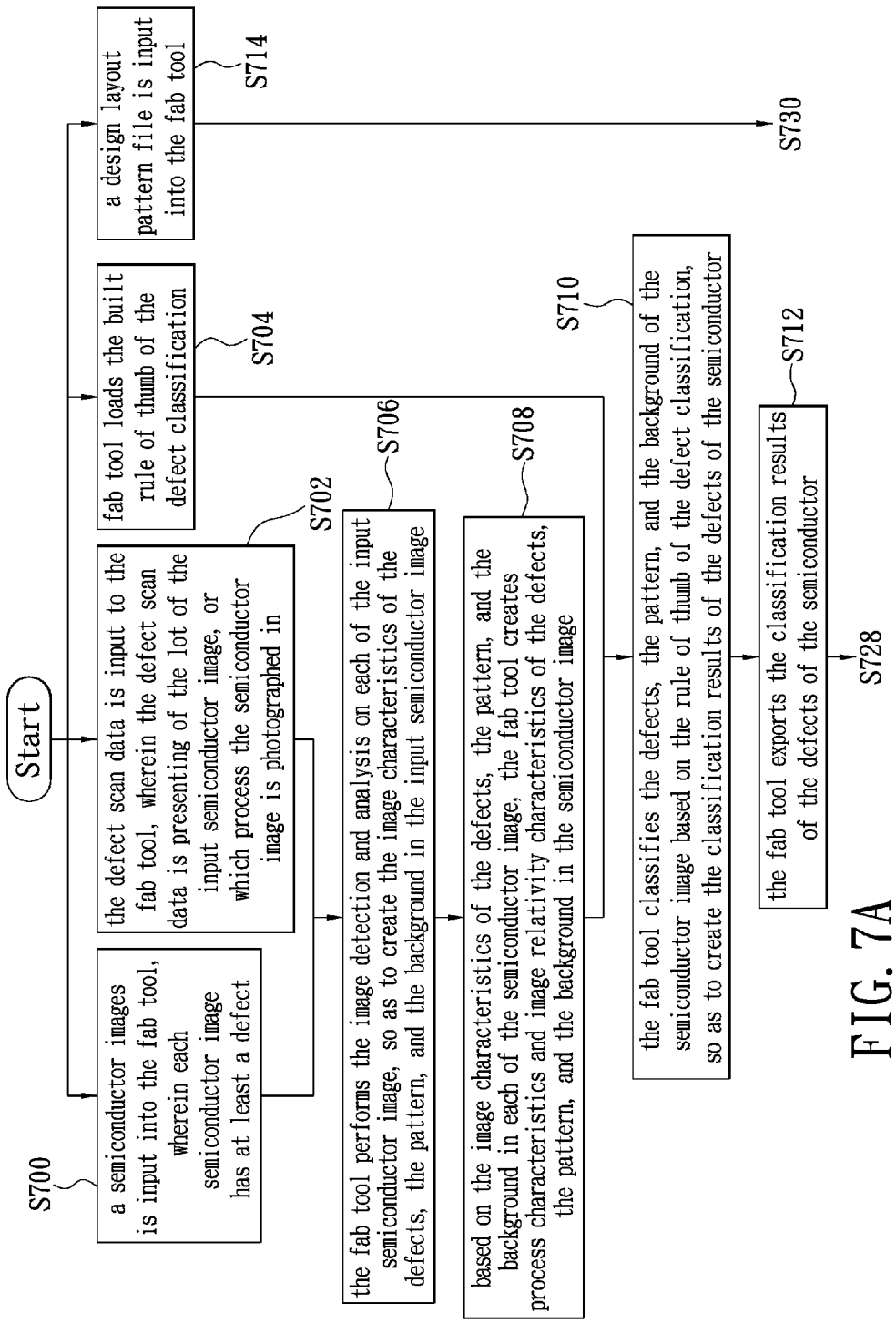

Referring to FIG. 7A and FIG. 7B, FIG. 7A and FIG. 7B are respectively the upper part and the lower part of the flow chart of a method for judging the killer defect based on the built rule of thumb of the defect classification and CAA according to an exemplary embodiment of the present disclosure. Being different from the method for judging the killer defect based on the built rule of thumb of the defect classification and CAA in FIG. 5A and FIG. 5B, the method for judging the killer defect based on the built rule of thumb of the defect classification and CAA in FIG. 7A and FIG. 7B uses the design layout pattern file to judge the killer defect.

In FIG. 7A, steps S700 through S712 are respectively the same as steps S400 through S412 of FIG. 4, and descriptions of steps S700 through S712 are thus omitted. At step S714, a design layout pattern file is input into the fab tool.

In FIG. 7B, at step 728, the fab tool creates the defect contours of the defect and pattern contours of the semiconductor image. Next, at step S724, the fab tool performs a scale matching on the semiconductor image and the design layout pattern of design layout pattern file, so as to adjust the scale of the design layout pattern of design layout pattern file. Then, at step S726, the fab tool performs a pattern matching on the adjusted design layout pattern polygons and the semiconductor image, so as to locate the correct defect coordinates of the defects. Then, at step S730, the fab tool performs the CCA on the defect contour of the defects and the scaled design layout pattern polygons, so as to judge whether the killer defect exists in the semiconductor.

To sum up, the exemplary embodiments of the present disclosure provides a method for building a rule of thumb of the defect classification and methods for classifying the defect and judging the killer defect based on the rule of thumb and CAA. These methods can be applied in the fab tool, and thus the fab can increase efficiency and throughput several times and reduce yield learning cycle time, while the fab classifies the defects and judges the killer defect. Furthermore, the methods for judging the killer defect based on the rule of thumb and CAA can be performed regardless of the design layout pattern file.

In order to further understand the techniques, means and effects the present disclosure, the following detailed descriptions and appended drawings are hereby referred, such that, through which, the purposes, features and aspects of the present disclosure can be thoroughly and concretely appreciated; however, the appended drawings are merely provided for reference and illustration, without any intention to be used for limiting the present disclosure.

What is claimed is:

1. A method for judging a killer defect based on a rule of thumb of defect classification and critical area analysis (CAA), applied in a fab tool, wherein the rule of thumb of the defect classification is built by a method for building the rule of thumb of the defect classification, wherein the method for building the rule of thumb of the defect classification comprises:

inputting multiple defect classification images with killer defects of examples into the fab tool;

inputting all material information of processes associated with the defect, the pattern, and the background into the fab tool;

performing an image detection and analysis on each of input images, so as to create image characteristics of the defects, the pattern, and the background in each of the input images, wherein the input images comprises the defect classification images with killer defects of examples;

based on the image characteristics of the defects, the pattern, and the background in each of the input images, creating process characteristics and image relativity characteristics of the defects, the pattern, and the background in each of the input images; and building the rule of thumb of the defect classification based on the process characteristics, the image characteristics, and the image relativity characteristics of the defects, the pattern, and the background in each of the input images; and the method for judging a killer defect based on a rule of thumb of defect classification and CAA comprising:

inputting a semiconductor image into the fab tool, wherein the semiconductor image has at least a defect;

inputting a defect scan data into the fab tool;

loading the rule of thumb of the defect classification;

performing an image detection and analysis on the input semiconductor image, so as to obtain the image characteristics of the defects, the pattern, and the background in the semiconductor image;

based on the image characteristics of the defects, the pattern, and the background in the semiconductor image, creating process characteristics and image relativity characteristics of the defects, the pattern, and the background in the semiconductor image;

classifying the defects, the pattern, and the background of the semiconductor image based on the rule of thumb of the defect classification, so as to create the classification results of the defects of the semiconductor;

inputting typical defect type and the killer judgment knowledge into the fab tool;

based on the typical defect type and the killer judgment knowledge and the classification results of the defects, creating image pattern contours inside a defect area, image pattern contours outside the defect area, and a defect contour of the defects;

recovering the image pattern contours inside the defect area;

merging the recovered image pattern contours inside the defect area and the image pattern contours outside the defect area, so as to create image pattern contours of layout polygons;

performing CAA based on the defect contour of the defects and the merged image pattern contours, so as to create a CAA result; and judging whether the killer defect exists in the semiconductor according to the CAA result.

2. The method for judging a killer defect based on a rule of thumb of defect classification and CAA according to claim 1, wherein fab tool removes the defect contour of the defects and the image pattern contours outside defect area, so as to extract the image pattern contours inside defect area, and the fab tool extends and connects each two of the disconnected ends in the image pattern contours inside defect area, so as to recover the image pattern contours inside defect area.

3. A method for judging a killer defect based on a rule of thumb of defect classification and CAA, applied in a fab tool, wherein the rule of thumb of the defect classification is built by a method for building the rule of thumb of the defect classification, wherein the method for building the rule of thumb of the defect classification comprises:

inputting multiple defect classification images with killer defects of examples into the fab tool;

inputting all material information of processes associated with the defect, the pattern, and the background into the fab tool;

performing an image detection and analysis on each of input images, so as to create image characteristics of the defects, the pattern, and the background in each of the input images, wherein the input images comprises the defect classification images with killer defects of examples;

based on the image characteristics of the defects, the pattern, and the background in each of the input images, creating process characteristics and image relativity characteristics of the defects, the pattern, and the background in each of the input images; and building the rule of thumb of the defect classification based on the process characteristics, the image characteristics, and the image relativity characteristics of the defects, the pattern, and the background in each of the input images; and the method for judging a killer defect based on a rule of thumb of defect classification and CAA comprising:

inputting a semiconductor image into the fab tool, wherein the semiconductor image has at least a defect;

inputting a defect scan data into the fab tool;

loading the rule of thumb of the defect classification;

performing an image detection and analysis on the input semiconductor image, so as to obtain the image characteristics of the defects, the pattern, and the background in the semiconductor image;

based on the image characteristics of the defects, the pattern, and the background in the semiconductor image, creating process characteristics and image relativity characteristics of the defects, the pattern, and the background in the semiconductor image;

classifying the defects, the pattern, and the background of the semiconductor image based on the rule of thumb of the defect classification, so as to create the classification results of the defects of the semiconductor;

inputting a design layout pattern file into the fab tool;

creating defect and pattern contours of the semiconductor image;

performing a scale matching on the semiconductor image and the design layout pattern of design layout pattern file, so as to adjust a scale of the design layout pattern of design layout pattern file;

performing a pattern matching on the adjusted design layout pattern polygons and the semiconductor image, so as to locate correct defect coordinates of the defects; and performing a critical area analysis on the defect contour of the defects and the scaled design layout pattern polygons, so as to judge whether the killer defect exists in the semiconductor.

4. The method for judging a killer defect based on a rule of thumb of defect classification and CAA according to claim 3, wherein fab tool removes the defect contour of the defects and the image pattern contours outside defect area, so as to extract the image pattern contours inside defect area, and the fab tool extends and connects each two of the disconnected ends in the image pattern contours inside defect area, so as to recover the image pattern contours inside defect area.

\* \* \* \* \*